US012725255B2

(12) United States Patent
Hirahara

(10) Patent No.: US 12,725,255 B2
(45) Date of Patent: Sep. 1, 2026

(54) IMAGE PROCESSING APPARATUS, IMAGE PROCESSING METHOD, AND IMAGE PROCESSING PROGRAM

(71) Applicant: FUJIFILM Corporation, Tokyo (JP)

(72) Inventor: Nobuyuki Hirahara, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 267 days.

(21) Appl. No.: 18/596,657

(22) Filed: Mar. 6, 2024

(65) Prior Publication Data

US 2024/0331147 A1 Oct. 3, 2024

(30) Foreign Application Priority Data

Mar. 28, 2023 (JP) ................................ 2023-051615

(51) Int. Cl.

| | |
|---|---|
| ***G06T 7/00*** | (2017.01) |
| ***G06T 5/50*** | (2006.01) |
| ***G06T 7/50*** | (2017.01) |
| ***G06V 10/46*** | (2022.01) |
| ***G06V 10/56*** | (2022.01) |
| ***G16H 30/40*** | (2018.01) |

(52) U.S. Cl.

CPC .............. *G06T 7/0012* (2013.01); *G06T 5/50* (2013.01); *G06T 7/50* (2017.01); *G06V 10/46* (2022.01); *G06V 10/56* (2022.01); *G16H 30/40* (2018.01); *G06T 2207/20221* (2013.01); *G06T 2207/30096* (2013.01)

(58) Field of Classification Search

CPC ............................... G06T 7/0012–0016; G06T 2207/30004–30104; G06T 5/50; G06V 10/56; G06V 10/46

See application file for complete search history.

(56) References Cited

U.S. PATENT DOCUMENTS

2003/0210813 A1* 11/2003 Oosawa ................ G06T 7/0012 382/130
2010/0220914 A1* 9/2010 Iwase .................... G06T 7/0012 382/131
2016/0270753 A1* 9/2016 Kawamura ............ G16H 50/30
2018/0263226 A1* 9/2018 Doiron ................... C07K 14/82
2019/0057504 A1 2/2019 Kobayashi
2019/0307410 A1* 10/2019 Morita .................... G06F 9/542
2022/0398735 A1* 12/2022 Rosenblum ............... G06T 7/35
2023/0274439 A1* 8/2023 Preuhs ...................... G06T 5/77 382/128
2024/0008801 A1* 1/2024 Kaufman ............... A61B 5/004

FOREIGN PATENT DOCUMENTS

JP 2019033966 3/2019
JP 2021087729 6/2021
KR 20220103852 A * 7/2022 ........... G06N 3/0455

OTHER PUBLICATIONS

Liyun Sun et al An Adversarial Learning Approach to Medical Image Synthesis for Lesion Detection IEEE 2020 (Year: 2020).*

* cited by examiner

*Primary Examiner* — Sean T Motsinger
(74) *Attorney, Agent, or Firm* — JCIPRNET

(57) ABSTRACT

An image processing apparatus generates an estimated medical image in which a state in which an abnormality candidate region, which is a region including a candidate for an abnormality, in a medical image, does not exist is estimated, and performs control of displaying information regarding a difference between the medical image and the estimated medical image.

15 Claims, 7 Drawing Sheets

1
12
IMAGING APPARATUS
18
10
IMAGE PROCESSING APPARATUS
14
IMAGE STORAGE SERVER

THERE IS POSSIBILITY THAT TAIL PART OF PANCREAS IS MORE ATROPHIED THAN NORMAL.

IMAGE PROCESSING APPARATUS, IMAGE PROCESSING METHOD, AND IMAGE PROCESSING PROGRAM

CROSS-REFERENCE TO RELATED APPLICATIONS

This application claims priority from Japanese Patent Application No. 2023-051615, filed on Mar. 28, 2023, the entire disclosure of which is incorporated herein by reference.

BACKGROUND

1. Technical Field

The present disclosure relates to an image processing apparatus, an image processing method, and an image processing program.

2. Description of the Related Art

JP2019-033966A discloses a technique of performing image analysis of a medical image using a trained discriminator and calculating a normality as a probability that a subject corresponds to any of a plurality of types of lesion patterns.

JP2021-087729A discloses a technique of calculating a malignancy of various lesions in each region of a medical image and generating a malignancy map for each type of the lesion.

SUMMARY

In diagnosis of a lesion such as a pancreatic cancer, for example, a medical image interpreter may determine whether or not the lesion has occurred based on an abnormality such as a shape change and a property change of a peripheral portion of the lesion due to occurrence of the lesion in the medical image. In this case, in a case in which a difference between the medical image to be interpreted and a medical image of the same patient in a case in which it is assumed that there is no candidate for an abnormality such as a lesion, a shape change, and a property change can be presented to the interpreter, it is possible to appropriately support interpretation of the medical image by the interpreter.

The present disclosure has been made in view of the above circumstances, and an object of the present disclosure is to provide an image processing apparatus, an image processing method, and an image processing program capable of presenting a difference between a medical image to be interpreted and a medical image in which a candidate for an abnormality does not exist.

According to a first aspect, there is provide an image processing apparatus comprising: at least one processor, in which the processor generates an estimated medical image in which a state in which an abnormality candidate region, which is a region including a candidate for an abnormality, in a medical image, does not exist is estimated, and performs control of displaying information regarding a difference between the medical image and the estimated medical image.

A second aspect provides the image processing apparatus according to the first aspect, in which the processor performs, as the control, control of displaying the medical image and the estimated medical image.

A third aspect provides the image processing apparatus according to the first aspect or the second aspect, in which the processor performs, as the control, control of displaying the medical image and information indicating the difference between the medical image and the estimated medical image.

A fourth aspect provides the image processing apparatus according to the third aspect, in which the processor performs, as the control, control of superimposing and displaying, on the medical image, an image of which a color is made different depending on a value indicating a difference between the abnormality candidate region of the medical image and a region of the estimated medical image corresponding to the abnormality candidate region.

A fifth aspect provides the image processing apparatus according to any one of the first aspect to fourth aspect, in which the processor performs, as the control, control of displaying a text indicating the difference between the medical image and the estimated medical image.

A sixth aspect provides the image processing apparatus according to any one of the first aspect to the fifth aspect, in which the processor performs, as the control, control of displaying a contour of the abnormality candidate region of the medical image and a contour of a region of the estimated medical image corresponding to the abnormality candidate region in a superimposed manner.

A seventh aspect provides the image processing apparatus according to any one of the first aspect to the sixth aspect, in which the processor performs, as the control, control of generating an image using volume rendering or surface rendering for each of the abnormality candidate region of the medical image and a region of the estimated medical image corresponding to the abnormality candidate region, and displaying the generated images in parallel or in a superimposed manner.

An eighth aspect provides the image processing apparatus according to any one of the first aspect to the seventh aspect, in which the processor extracts the abnormality candidate region from the medical image.

A ninth aspect provides the image processing apparatus according to any one of the first aspect to the seventh aspect, in which the processor receives designation of the abnormality candidate region by a user.

A tenth aspect provides the image processing apparatus according to any one of the first aspect to the ninth aspect, in which the candidate for the abnormality is a lesion.

An eleventh aspect provides the image processing apparatus according to any one of the first aspect to the tenth aspect, in which the candidate for the abnormality is a portion that is generated around a lesion and that is abnormal in at least one of a shape or a property.

A twelfth aspect provides the image processing apparatus according to any one of the first aspect to the eleventh aspect, in which the medical image is a medical image in which a pancreas is captured.

A thirteenth aspect provides the image processing apparatus according to the twelfth aspect, in which the abnormality candidate region is a region including the candidate for the abnormality among a head part region, a body part region, and a tail part region of the pancreas.

A fourteenth aspect provides the image processing apparatus according to any one of the first aspect to the thirteenth aspect, in which the processor generates an estimated image of the abnormality candidate region from a region other than the abnormality candidate region in a target anatomical region in the medical image, and generates an image in which the abnormality candidate region in the medical image is combined with the estimated image, as the estimated medical image.

According to a fifteenth aspect, there is provided an image processing method executed by a processor of an image processing apparatus, the method comprising: generating an estimated medical image in which a state in which an abnormality candidate region, which is a region including a candidate for an abnormality, in a medical image, does not exist is estimated; and performing control of displaying information regarding a difference between the medical image and the estimated medical image.

According to a sixteenth aspect, there is provided an image processing program for executing a processor of an image processing apparatus to execute: generating an estimated medical image in which a state in which an abnormality candidate region, which is a region including a candidate for an abnormality, in a medical image, does not exist is estimated; and performing control of displaying information regarding a difference between the medical image and the estimated medical image.

According to the present disclosure, it is possible to present a difference between a medical image to be interpreted and a medical image in which a candidate for an abnormality does not exist.

DETAILED DESCRIPTION

Hereinafter, examples of an embodiment for implementing the technique of the present disclosure will be described in detail with reference to the drawings.

Figures 1, 2:
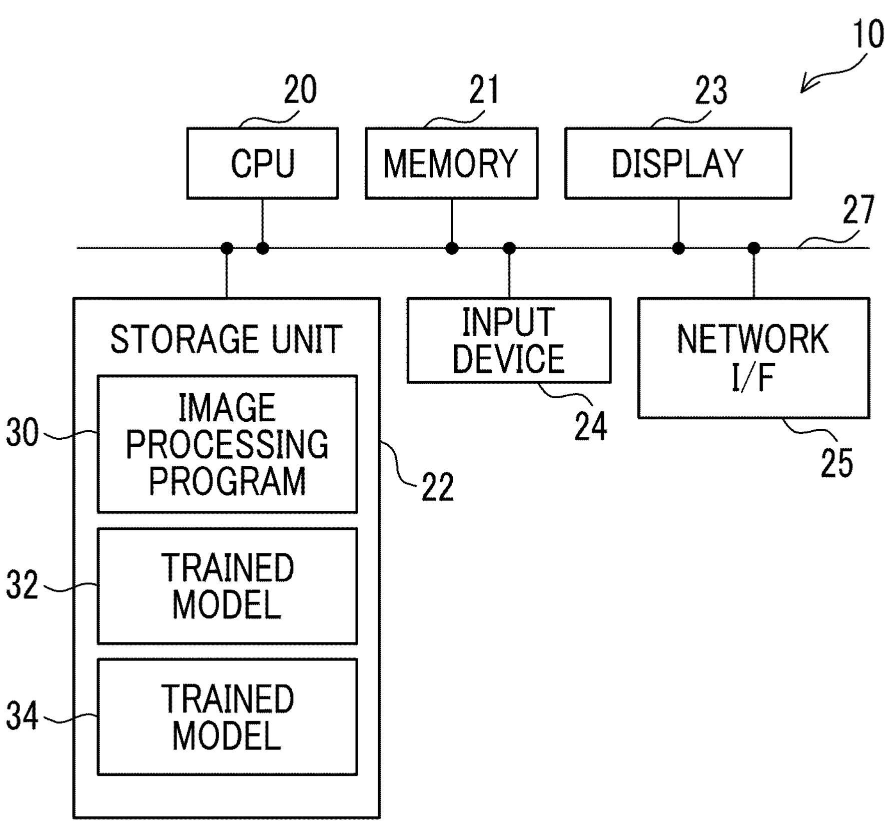
FIG. 1 is a block diagram showing a schematic configuration of a medical information system.
FIG. 2 is a block diagram showing an example of a hardware configuration of an image processing apparatus.

First, a configuration of a medical information system 1 according to the present embodiment will be described with reference to FIG. 1. As shown in FIG. 1, the medical information system 1 includes an image processing apparatus 10, an imaging apparatus 12, and an image storage server 14. The image processing apparatus 10, the imaging apparatus 12, and the image storage server 14 are connected to each other in a communicable manner via a wired or wireless network 18. The image processing apparatus 10 is, for example, a computer such as a personal computer or a server computer.

The imaging apparatus 12 is an apparatus that generates a medical image showing a diagnosis target part of a subject by imaging the part. Examples of the imaging apparatus 12 include a simple X-ray imaging apparatus, an endoscope apparatus, a computed tomography (CT) apparatus, a magnetic resonance imaging (MRI) apparatus, and a positron emission tomography (PET) apparatus. In the present embodiment, an example will be described in which the imaging apparatus 12 is a CT device and the diagnosis target part is an abdomen. That is, the imaging apparatus 12 according to the present embodiment generates a CT image of the abdomen of the subject as a three-dimensional medical image formed of a plurality of tomographic images. Accordingly, the medical image according to the present embodiment is a medical image in which the pancreas is captured. The medical image generated by the imaging apparatus 12 is transmitted to the image storage server 14 via the network 18 and stored by the image storage server 14.

The image storage server 14 is a computer that stores and manages various types of data, and comprises a large-capacity external storage device and database management software. The image storage server 14 receives the medical image generated by the imaging apparatus 12 via the network 18, and stores and manages the received medical image. A storage format of image data by the image storage server 14 and the communication with another device via the network 18 are based on a protocol such as digital imaging and communication in medicine (DICOM).

Next, a hardware configuration of the image processing apparatus 10 according to the present embodiment will be described with reference to FIG. 2. As shown in FIG. 2, the image processing apparatus 10 includes a central processing unit (CPU) 20, a memory 21 as a temporary storage region, and a non-volatile storage unit 22. In addition, the image processing apparatus 10 includes a display 23 such as a liquid crystal display, an input device 24 such as a keyboard and a mouse, and a network interface (I/F) 25 that is connected to the network 18. The CPU 20, the memory 21, the storage unit 22, the display 23, the input device 24, and the network I/F 25 are connected to a bus 27. The CPU 20 is an example of a processor according to the technique of the present disclosure.

The storage unit 22 is realized by a hard disk drive (HDD), a solid state drive (SSD), a flash memory, or the like. An image processing program 30 is stored in the storage unit 22 as a storage medium. The CPU 20 reads out the image processing program 30 from the storage unit 22, expands the image processing program 30 in the memory 21, and executes the expanded image processing program 30.

Incidentally, in a case in which an abnormality has occurred in an anatomical region in a medical image, it is possible to effectively support interpretation of the medical image by an interpreter in a case in which a medical image in which a state in which the abnormality does not exist is estimated can be generated. The image processing apparatus 10 according to the present embodiment has a function of generating and presenting a medical image in which a state in which an abnormality does not exist is estimated, in order to effectively support the interpretation of the medical image by the interpreter. In the present embodiment, an example in which the pancreas is applied as the anatomical region to be processed will be described.

In order to realize the above-described function, a trained model 32 and a trained model 34 are stored in the storage unit 22. The trained model 32 is a model for extracting a region including a candidate for an abnormality (hereinafter, referred to as an "abnormality candidate region") in a medical image. The trained model 32 is configured by, for example, a convolutional neural network (CNN). The trained model 32 is a model that is trained through machine learning using, for example, a large number of combinations of a medical image including a candidate for an abnormality and information specifying the abnormality candidate region in the medical image as learning data. The candidate for the abnormality in the present embodiment includes, for example, a lesion such as a pancreatic cancer. In addition, the candidate for the abnormality in the present embodiment includes, in addition to a lesion, a portion that is generated around the lesion and that is abnormal in at least one of a shape or a property. This abnormal portion is also referred to as an indirect finding. For example, examples of the indirect finding suspected to be a pancreatic cancer include a shape abnormality such as partial atrophy and swelling in the pancreas.

Figure 3:
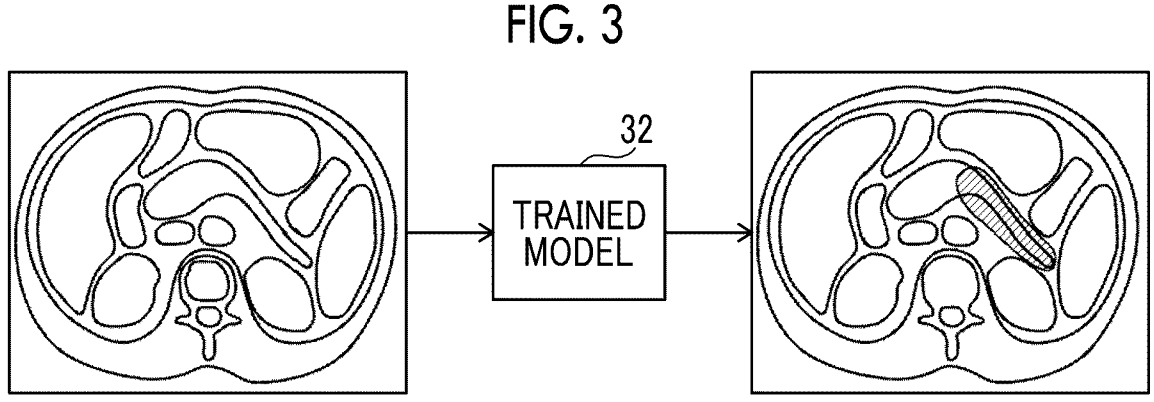
FIG. 3 is a diagram for describing a first trained model.

As shown in FIG. 3 as an example, a medical image is input to the trained model 32. The trained model 32 detects an abnormality candidate region of the pancreas in the input medical image and outputs information specifying the abnormality candidate region. The information specifying the abnormality candidate region need only be information with which the abnormality candidate region can be specified. For example, the information specifying the abnormality candidate region may be information representing a voxel position of the abnormality candidate region in the medical image or an image in which the abnormality candidate region in the medical image is filled with a preset color, for example. In the example of FIG. 3, partial atrophy is detected as the candidate for the abnormality of the pancreas, and the abnormality candidate region is represented by a region filled with diagonal lines.

The trained model 34 is a model for generating an estimated medical image in which a state in which the abnormality candidate region in the medical image does not exist is estimated. The trained model 34 is configured by, for example, a CNN. The trained model 34 is a model that is trained through machine learning using, for example, a large number of combinations of a medical image including the abnormality candidate region, information specifying the abnormality candidate region in the medical image, and a medical image in a state in which the abnormality candidate region does not exist as learning data.

Figure 4:
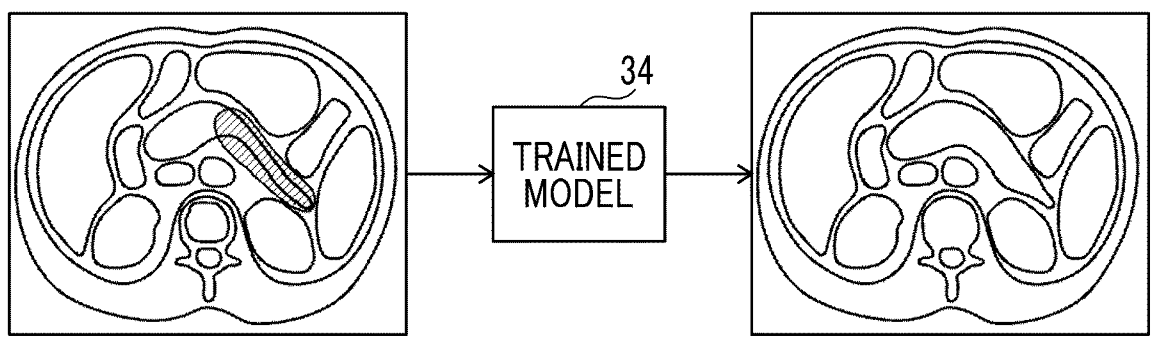
FIG. 4 is a diagram for describing a second trained model.

As shown in FIG. 4 as an example, the medical image and the information specifying the abnormality candidate region in the medical image are input to the trained model 34. The trained model 34 generates and outputs an estimated medical image in which a state in which the abnormality candidate region in the input medical image does not exist is estimated. In the example of FIG. 4, an estimated medical image in a state in which partial atrophy of the pancreas does not exist is generated.

Figure 5:
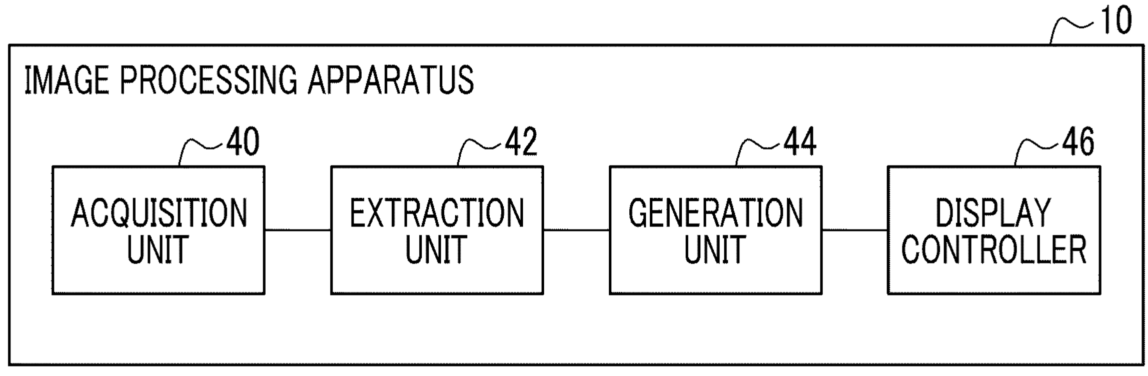
FIG. 5 is a block diagram showing an example of a functional configuration of the image processing apparatus.

Next, a functional configuration of the image processing apparatus 10 according to the present embodiment will be described with reference to FIG. 5. As shown in FIG. 5, the image processing apparatus 10 includes an acquisition unit 40, an extraction unit 42, a generation unit 44, and a display controller 46. The CPU 20 executes the image processing program 30 to function as the acquisition unit 40, the extraction unit 42, the generation unit 44, and the display controller 46.

The acquisition unit 40 acquires a medical image to be diagnosed (hereinafter, referred to as a "diagnosis target image") from the image storage server 14 via the network I/F 25.

Figure 6:
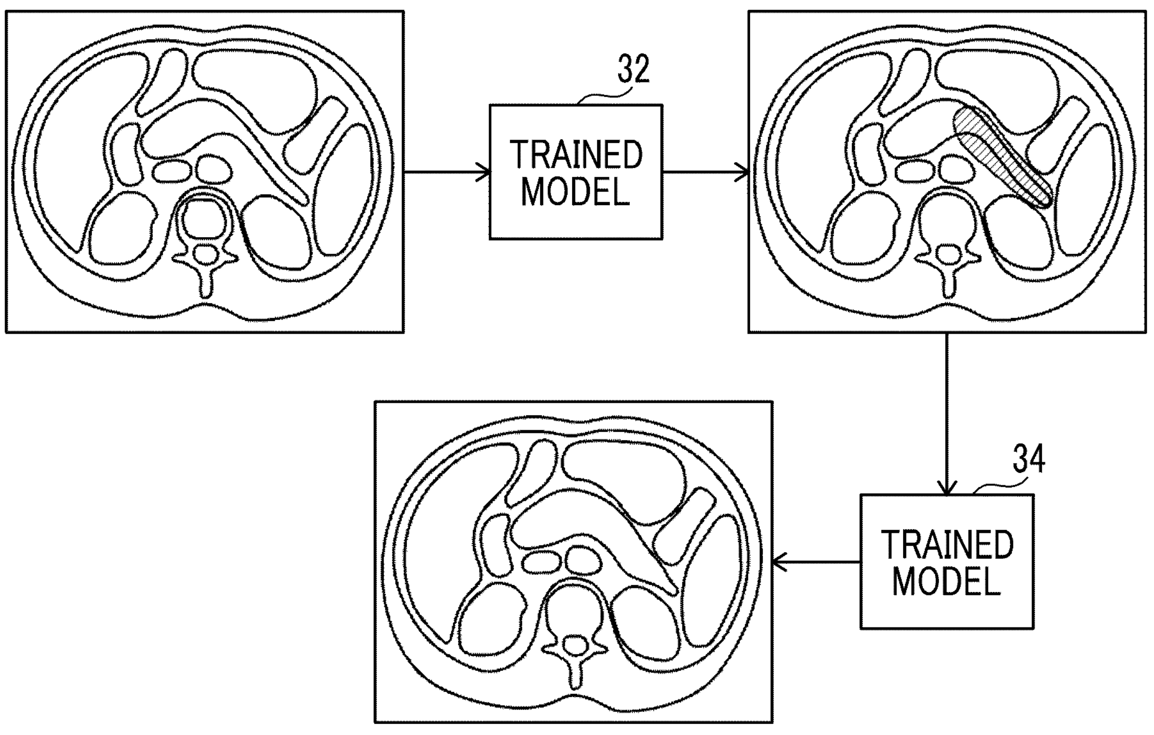
FIG. 6 is a diagram for describing a process of generating an estimated medical image.

The extraction unit 42 extracts an abnormality candidate region from the diagnosis target image acquired by the acquisition unit 40. Specifically, as shown in FIG. 6, the extraction unit 42 inputs the diagnosis target image to the trained model 32. The trained model 32 detects an abnormality candidate region of the pancreas in the input diagnosis target image and outputs information specifying the abnormality candidate region.

The abnormality candidate region may be designated by the user via the input device 24. In this case, the extraction unit 42 receives the designation of the abnormality candidate region by the user, and extracts the received abnormality candidate region from the diagnosis target image.

The generation unit 44 generates an estimated medical image in which a state in which the abnormality candidate region extracted by the extraction unit 42 in the diagnosis target image acquired by the acquisition unit 40 does not exist is estimated. Specifically, as shown in FIG. 6, the generation unit 44 inputs the diagnosis target image and the information specifying the abnormality candidate region, which is output from the trained model 32, to the trained model 34. The trained model 34 generates and outputs an estimated medical image in which a state in which the abnormality candidate region in the input diagnosis target image does not exist is estimated.

Figure 7:
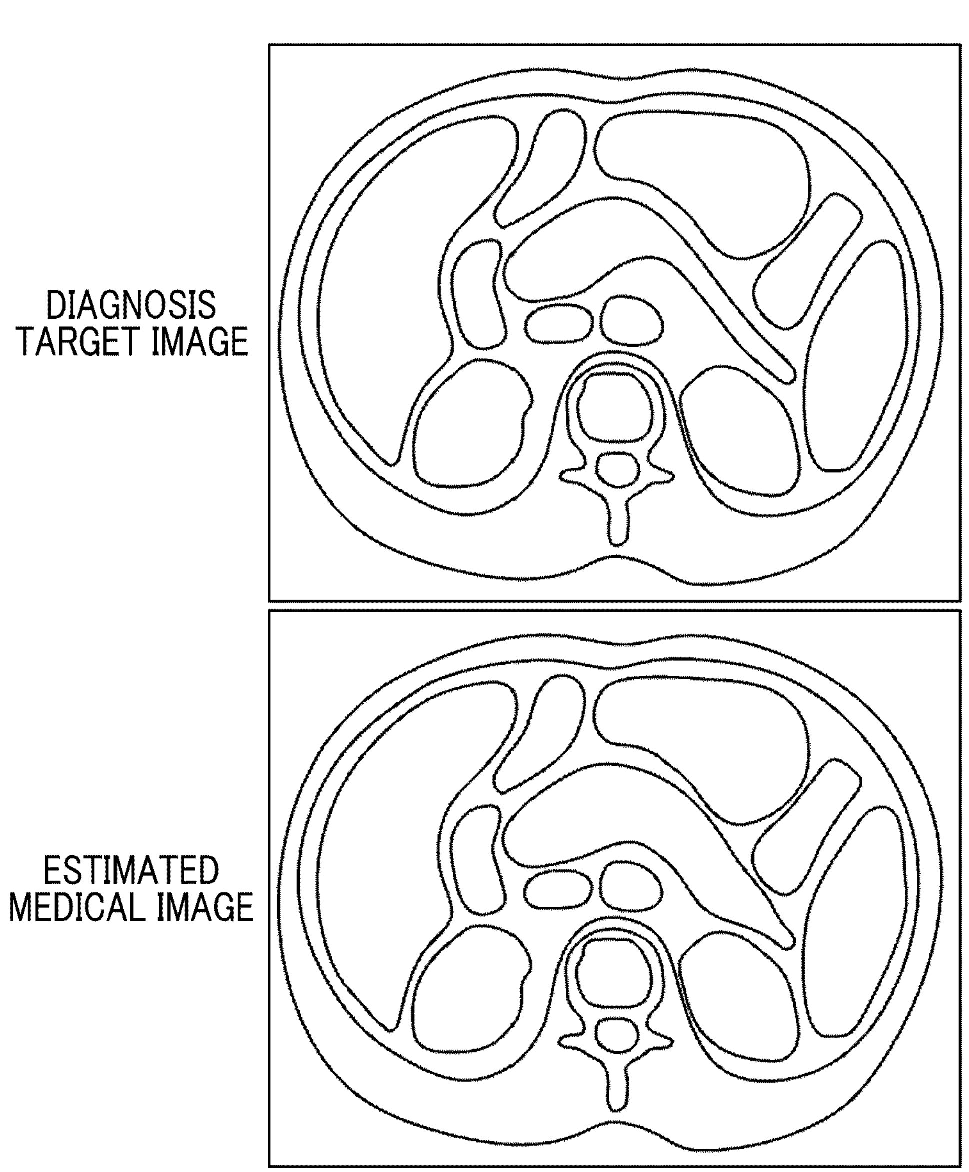
FIG. 7 is a diagram showing an example of a display screen.

The display controller 46 performs control of displaying information regarding a difference between the diagnosis target image acquired by the acquisition unit 40 and the estimated medical image generated by the generation unit 44. Specifically, as shown in FIG. 7 as an example, the display controller 46 performs control of displaying the diagnosis target image and the estimated medical image side by side on the display 23. As a result, the user can easily understand the difference between the diagnosis target image and the estimated medical image.

Figure 8:
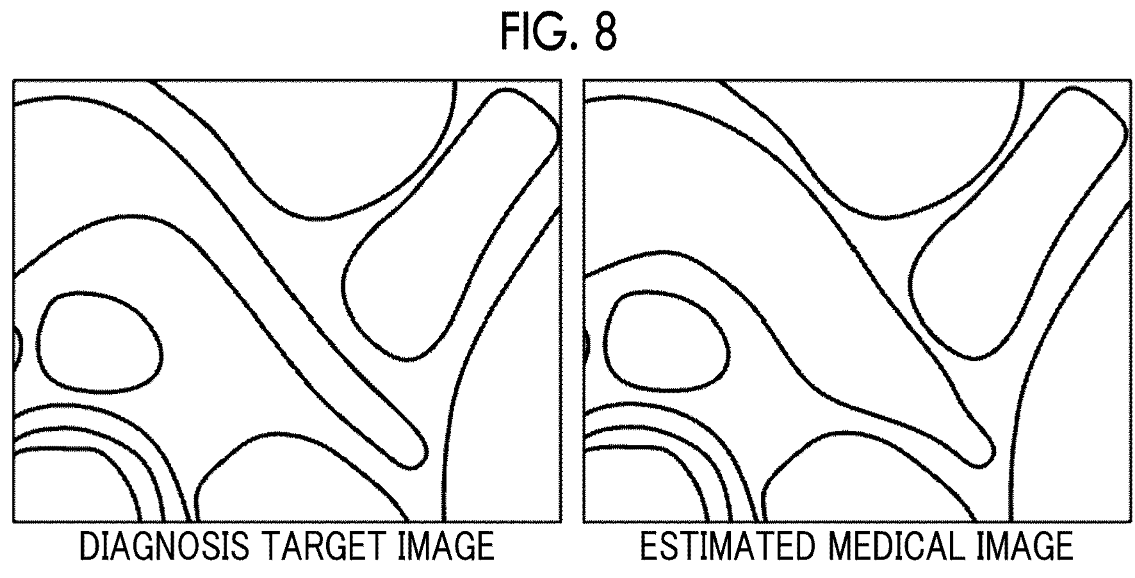
FIG. 8 is a diagram showing an example of a display screen according to a modification example.

As shown in FIG. 8, the display controller 46 may perform control of displaying the abnormality candidate region of the diagnosis target image and a region of the estimated medical image corresponding to the abnormality candidate region in an enlarged state side by side on the display 23. In the example of FIG. 8, a region of the diagnosis target image in which the atrophy of the pancreas exists and a region of the estimated medical image, in which the atrophy of the pancreas is resolved, corresponding to the region in which the atrophy exists are shown in an enlarged state.

Next, an operation of the image processing apparatus 10 according to the present embodiment will be described with reference to FIG. 9. The CPU 20 executes the image processing program 30 to execute a diagnosis support process shown in FIG. 9. The diagnosis support process shown in FIG. 9 is executed, for example, in a case in which an instruction to start an execution is input by the user.

Figure 9:
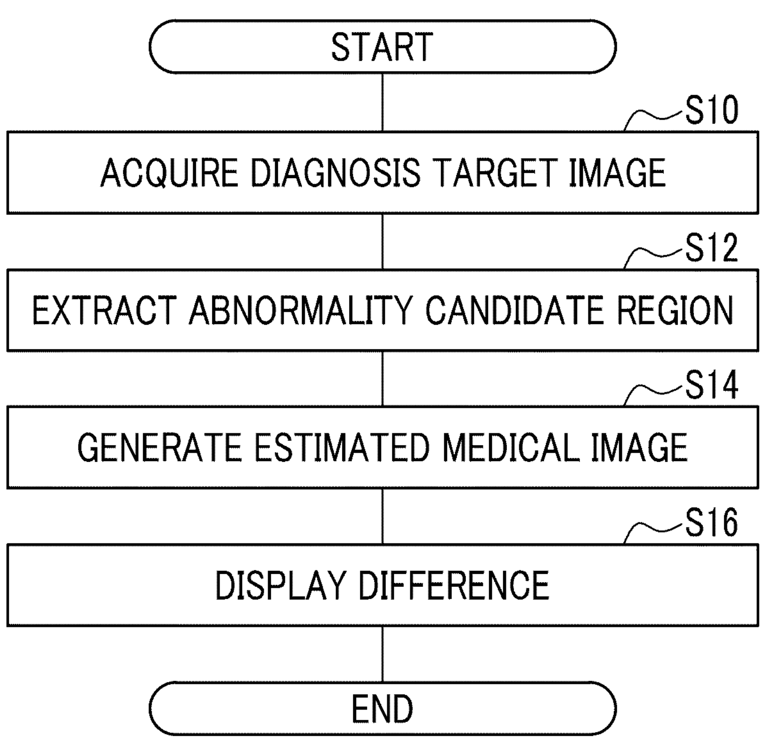
FIG. 9 is a flowchart showing an example of a diagnosis support process.

In step S10 of FIG. 9, the acquisition unit 40 acquires the diagnosis target image from the image storage server 14 via the network I/F 25. In step S12, as described above, the extraction unit 42 inputs the diagnosis target image acquired in step S10 to the trained model 32 to extract the abnormality candidate region from the diagnosis target image.

In step S14, as described above, the generation unit 44 inputs the diagnosis target image acquired in step S10 and the information specifying the abnormality candidate region extracted in step S12 to the trained model 34. As a result, the generation unit 44 generates an estimated medical image in which a state in which the abnormality candidate region in the input diagnosis target image does not exist is estimated.

In step S16, as described above, the display controller 46 performs control of displaying information regarding a difference between the diagnosis target image acquired in step S10 and the estimated medical image generated in step S14. In a case in which the process of step S16 ends, the diagnosis support process ends.

As described above, according to the present embodiment, it is possible to present a difference between a medical image to be interpreted and a medical image in which a candidate for an abnormality does not exist, and as a result, it is possible to effectively support the interpretation of the medical image by the interpreter.

Figures 10, 11:
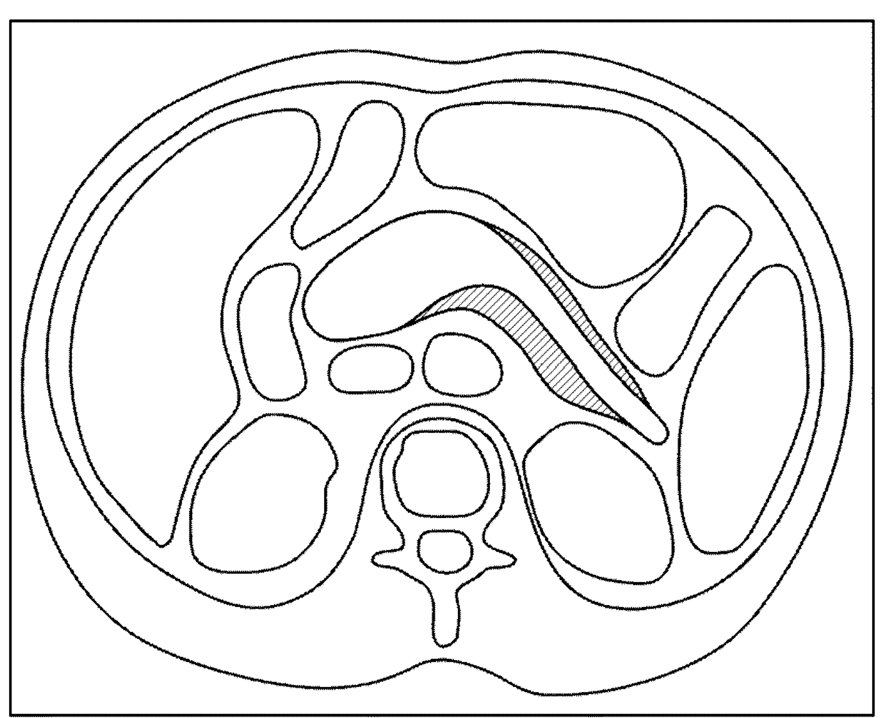
FIG. 10 is a diagram showing an example of a display screen according to a modification example.
FIG. 11 is a diagram showing an example of a display screen according to a modification example.

In the above embodiment, the display controller 46 may perform control of displaying the diagnosis target image and information indicating a difference between the diagnosis target image and the estimated medical image, as control of displaying information regarding a difference between the diagnosis target image and the estimated medical image. Specifically, as shown in FIG. 10, the display controller 46 may perform control of superimposing and displaying, on the diagnosis target image, an image of which a color is made different depending on a value indicating a difference between the abnormality candidate region of the diagnosis target image and a region of the estimated medical image corresponding to the abnormality candidate region. In the example of FIG. 10, a region of the difference between the abnormality candidate region of the diagnosis target image and the region of the estimated medical image corresponding to the abnormality candidate region is filled with diagonal lines. For example, the display controller 46 causes, for each voxel of the region of the diagonal lines, a color of the region closer to blue as a difference between the CT value of the diagnosis target image and the CT value of the estimated medical image is smaller, and causes the color of the region closer to red as the difference is larger.

In addition, in the above embodiment, as shown in FIG. 11, the display controller 46 may perform control of displaying a text indicating the difference between the diagnosis target image and the estimated medical image. FIG. 11 shows an example of a text in a case in which a tail part of the pancreas in the diagnosis target image is atrophied.

In addition, in the above embodiment, the display controller 46 may perform control of displaying a contour of the abnormality candidate region of the diagnosis target image and a contour of the region of the estimated medical image corresponding to the abnormality candidate region in a superimposed manner.

In addition, in the above embodiment, the display controller 46 may generate an image using volume rendering or surface rendering for each of the abnormality candidate region of the diagnosis target image and the region of the estimated medical image corresponding to the abnormality candidate region. In this case, the display controller 46 may perform control of displaying the generated images in parallel or control of displaying the generated images in a superimposed manner.

Figure 12:
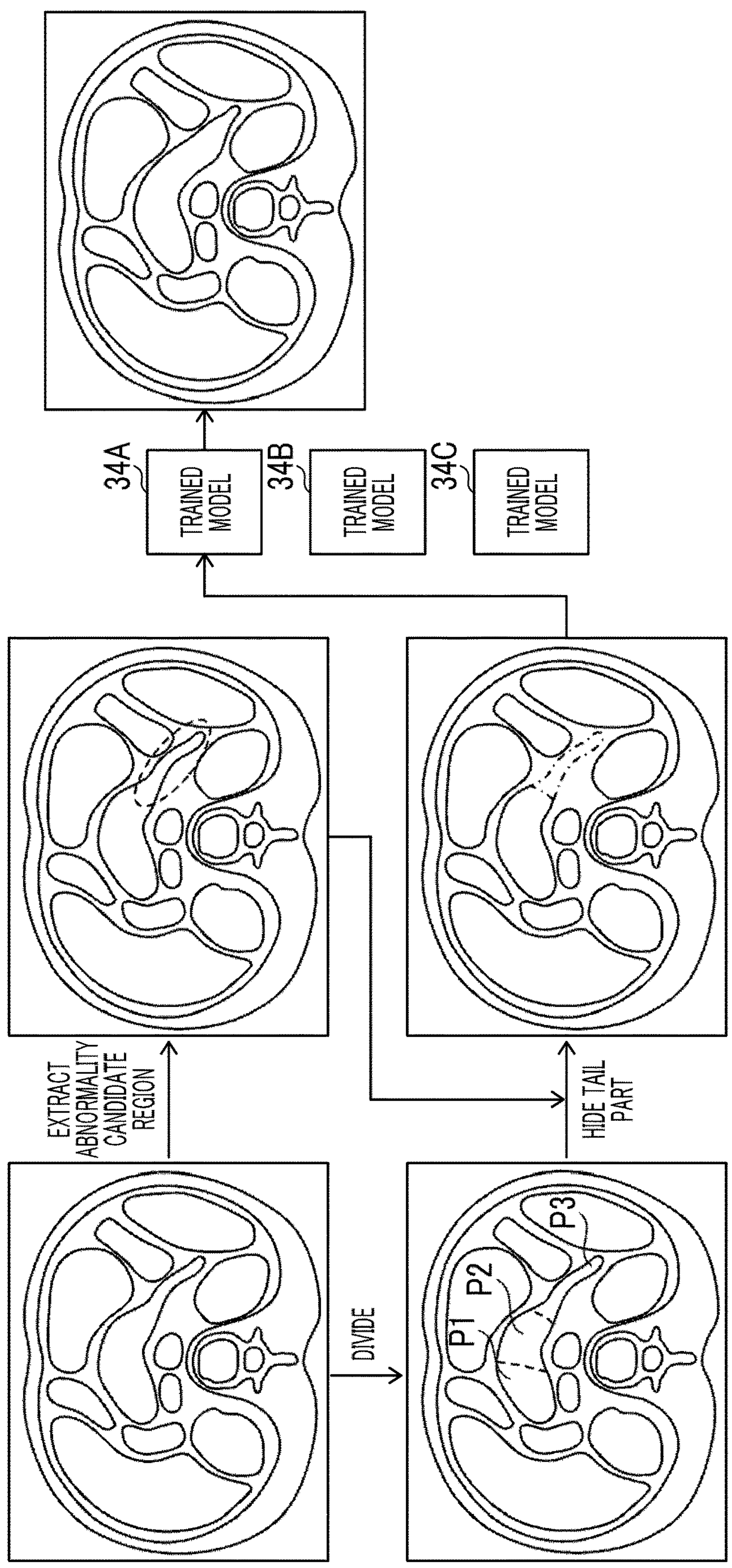
FIG. 12 is a diagram for describing a process of generating an estimated medical image according to a modification example.

In addition, in the above embodiment, as shown in FIG. 12, the CPU 20 may divide the pancreas as an example of the anatomical region included in the diagnosis target image into three partial regions of a head part P1, a body part P2, and a tail part P3. In this case, the extraction unit 42 extracts, as the abnormality candidate region, a region including a candidate for an abnormality among a region of the head part P1, a region of the body part P2, and a region of the tail part P3 of the pancreas from the diagnosis target image.

In this case, the generation unit 44 may generate an estimated image of the abnormality candidate region from a region other than the abnormality candidate region in the pancreas in the input diagnosis target image, generates an image obtained by combining the estimated image with the abnormality candidate region in the diagnosis target image. Specifically, as shown in FIG. 12, three trained models 34A, 34B, and 34C are prepared as the trained model 34. The trained model 34A is a model that generates an estimated image in which the tail part P3 of the pancreas in the input medical image is estimated based on the head part P1 and the body part P2 of the pancreas in the medical image, and generates an image in which the tail part P3 in the input medical image is combined with the estimated image. The trained model 34B is a model that generates an estimated image in which the body part P2 of the pancreas in the input medical image is estimated based on the head part P1 and the tail part P3 of the pancreas in the medical image, and generates an image in which the body part P2 in the input medical image is combined with the estimated image. The trained model 34C is a model that generates an estimated image in which the head part P1 of the pancreas in the input medical image is estimated based on the body part P2 and the tail part P3 of the pancreas in the medical image, and generates an image in which the head part P1 in the input medical image is combined with the estimated image.

In this case, the generation unit 44 executes image processing to hide the abnormality candidate region extracted by the extraction unit 42 in the diagnosis target image. Examples of the image processing include a process of filling a region to be hidden with a predetermined color such as a background color. In the example in FIG. 12, a region of the tail part P3, which is the region to be hidden by the image processing, is indicated by a one-dot chain line. Then, the generation unit 44 inputs the diagnosis target image, which has been subjected to the image processing to hide the abnormality candidate region, to the trained model 34 corresponding to the abnormality candidate region. The trained model 34 generates and outputs an estimated image of the abnormality candidate region from a region other than the abnormality candidate region in the pancreas in the input diagnosis target image, generates an image obtained by combining the estimated image with the abnormality candidate region in the diagnosis target image. FIG. 12 shows an example in which the tail part P3 surrounded by a broken line is extracted as the abnormality candidate region, the image processing to hide the tail part P3 is executed, and the diagnosis target image after the execution of the image processing is input to the trained model 34A to generate an estimated medical image.

In addition, in the above embodiment, as the trained model 34, a generative model called a generative adversarial network (GAN) may be applied.

In addition, in the above embodiment, a case in which the extraction unit 42 extracts the abnormality candidate region from the diagnosis target image using the trained model 32 has been described, but the present disclosure is not limited to this. For example, the extraction unit 42 may extract the abnormality candidate region from the diagnosis target image by a known method such as region growth, a contour extraction method, or extraction based on a rule.

In addition, in the above embodiment, a case in which the pancreas is applied as the anatomical region to be processed has been described, but the present disclosure is not limited to this. As the anatomical region to be processed, the liver may be applied, or the small intestine may be applied.

In the above embodiment, a case in which the trained models 32 and 34 are configured by the CNN has been described, but the present disclosure is not limited to this. The trained models 32 and 34 may be configured by a machine learning method other than the CNN.

In addition, in the embodiment, a case in which a CT image is applied as the diagnosis target image has been described, but the present disclosure is not limited to this. As the diagnosis target image, a medical image other than the CT image, such as a radiation image captured by a simple X-ray imaging apparatus and an MRI image captured by an MRI apparatus, may be applied.

The processes in steps S10 to S14 of the diagnosis support process according to the above embodiment may be executed before an instruction to start an execution is input by the user. In this case, in a case in which the user inputs an instruction to start an execution, step S16 is executed, and the screen is displayed.

In addition, in the above embodiment, for example, as hardware structures of processing units that execute various kinds of processing, such as the acquisition unit 40, the extraction unit 42, the generation unit 44, and the display controller 46, various processors shown below can be used. The various processors include, as described above, in addition to a CPU, which is a general-purpose processor that functions as various processing units by executing software (program), a programmable logic device (PLD) that is a processor of which a circuit configuration may be changed after manufacture, such as a field programmable gate array (FPGA), and a dedicated electrical circuit which is a processor having a circuit configuration specially designed to execute specific processing, such as an application specific integrated circuit (ASIC).

One processing unit may be configured of one of the various processors, or may be configured of a combination of the same or different kinds of two or more processors (for example, a combination of a plurality of FPGAs or a combination of the CPU and the FPGA). In addition, a plurality of processing units may be configured of one processor.

As an example in which a plurality of processing units are configured of one processor, first, as typified by a computer such as a client or a server, there is an aspect in which one processor is configured of a combination of one or more CPUs and software, and this processor functions as a plurality of processing units. Second, as typified by a system on chip (SoC) or the like, there is an aspect in which a processor that implements functions of the entire system including the plurality of processing units via one integrated circuit (IC) chip is used. As described above, various processing units are configured by using one or more of the various processors as a hardware structure.

Further, as the hardware structure of the various processors, more specifically, an electric circuit (circuitry) in which circuit elements such as semiconductor elements are combined may be used.

In the embodiment, an aspect has been described in which the image processing program 30 is stored (installed) in the storage unit 22 in advance, but the present disclosure is not limited to this. The image processing program 30 may be provided in an aspect in which the image processing program 30 is recorded in a recording medium, such as a compact disc read only memory (CD-ROM), a digital versatile disc read only memory (DVD-ROM), and a universal serial bus (USB) memory. In addition, the image processing program 30 may be downloaded from an external device via a network.

What is claimed is:

1. An image processing apparatus comprising:
at least one processor,
wherein the processor is configured to:
generate an estimated medical image in which a state in which an abnormality candidate region, which is a region including a candidate for an abnormality, in a medical image, does not exist is estimated, and
perform control of displaying information regarding a difference between the medical image and the estimated medical image,
wherein the processor is further configured to:
hide the abnormality candidate region in the medical image,
in response to hiding the abnormality candidate region in the medical image, generate an estimated image of the hidden abnormality candidate region from a region other than the abnormality candidate region in a target anatomical region in the medical image, and
generate an image in which the hidden abnormality candidate region in the medical image is combined with the estimated image, as the estimated medical image.

2. The image processing apparatus according to claim 1, wherein the processor is configured to perform, as the control, control of displaying the medical image and the estimated medical image.

3. The image processing apparatus according to claim 1, wherein the processor is configured to perform, as the control, control of displaying the medical image and information indicating the difference between the medical image and the estimated medical image.

4. The image processing apparatus according to claim 3, wherein the processor is configured to perform, as the control, control of superimposing and displaying, on the medical image, an image of which a color is made different depending on a value indicating a difference between the abnormality candidate region of the medical image and a region of the estimated medical image corresponding to the abnormality candidate region.

5. The image processing apparatus according to claim 1, wherein the processor is configured to perform, as the control, control of displaying a text indicating the difference between the medical image and the estimated medical image.

6. The image processing apparatus according to claim 1, wherein the processor is configured to perform, as the control, control of displaying a contour of the abnormality candidate region of the medical image and a contour of a region of the estimated medical image corresponding to the abnormality candidate region in a superimposed manner.

7. The image processing apparatus according to claim 1, wherein the processor is configured to perform, as the control, control of generating an image using volume rendering or surface rendering for each of the abnormality candidate region of the medical image and a region of the estimated medical image corresponding to the abnormality candidate region, and displaying the generated images in parallel or in a superimposed manner.

8. The image processing apparatus according to claim 1, wherein the processor is configured to extract the abnormality candidate region from the medical image.

9. The image processing apparatus according to claim 1, wherein the processor is configured to receive designation of the abnormality candidate region by a user.

10. The image processing apparatus according to claim 1, wherein the candidate for the abnormality is a lesion.

11. The image processing apparatus according to claim 1, wherein the candidate for the abnormality is a portion that is generated around a lesion and that is abnormal in at least one of a shape or a property.

12. The image processing apparatus according to claim 1, wherein the medical image is a medical image in which a pancreas is captured.

13. The image processing apparatus according to claim 12, wherein the abnormality candidate region is a region including the candidate for the abnormality among a head part region, a body part region, and a tail part region of the pancreas.

14. An image processing method executed by a processor of an image processing apparatus, the method comprising:

generating an estimated medical image in which a state in which an abnormality candidate region, which is a region including a candidate for an abnormality, in a medical image, does not exist is estimated;

hiding the abnormality candidate region in the medical image;

in response to hiding the abnormality candidate region in the medical image, generating an estimated image of the hidden abnormality candidate region from a region other than the abnormality candidate region in a target anatomical region in the medical image;

generating an image in which the hidden abnormality candidate region in the medical image is combined with the estimated image, as the estimated medical image; and performing control of displaying information regarding a difference between the medical image and the estimated medical image.

15. A non-transitory computer-readable storage medium storing an image processing program for executing a processor of an image processing apparatus to execute:

generating an estimated medical image in which a state in which an abnormality candidate region, which is a region including a candidate for an abnormality, in a medical image, does not exist is estimated;

hiding the abnormality candidate region in the medical image;

in response to hiding the abnormality candidate region in the medical image, generating an estimated image of the hidden abnormality candidate region from a region other than the abnormality candidate region in a target anatomical region in the medical image;

generating an image in which the hidden abnormality candidate region in the medical image is combined with the estimated image, as the estimated medical image; and performing control of displaying information regarding a difference between the medical image and the estimated medical image.

* * * * *